US008152693B2

(12) United States Patent
Nurmela et al.

(10) Patent No.: US 8,152,693 B2
(45) Date of Patent: Apr. 10, 2012

(54) EXERCISE DATA DEVICE, SERVER, SYSTEM AND METHOD

(75) Inventors: Marja-Leena Nurmela, Routio (FI); Heini Tuorila, Oulu (FI); Dominick Reed, Brinkley (GB)

(73) Assignee: Nokia Corporation, Espoo (FI)

( * ) Notice: Subject to any disclaimer, the term of this patent is extended or adjusted under 35 U.S.C. 154(b) by 339 days.

(21) Appl. No.: 11/429,914

(22) Filed: May 8, 2006

(65) Prior Publication Data
US 2007/0260482 A1 Nov. 8, 2007

(51) Int. Cl.
A63B 71/00 (2006.01)

(52) U.S. Cl. .......................................... 482/8; 702/149

(58) Field of Classification Search ................... 482/1–9; 702/213, 214, 215, 216, 142, 149, 160, 176; 701/213, 214, 215, 216
See application file for complete search history.

(56) References Cited

U.S. PATENT DOCUMENTS

| 5,335,188 | A  |   | 8/1994  | Brisson |
|-----------|----|---|---------|---------|
| 5,553,007 | A  | * | 9/1996  | Brisson .......................... 702/182 |
| 6,002,982 | A  | * | 12/1999 | Fry ................................. 701/213 |
| 6,013,007 | A  |   | 1/2000  | Root et al. |
| 6,066,075 | A  | * | 5/2000  | Poulton .............................. 482/8 |
| 6,148,262 | A  | * | 11/2000 | Fry ................................. 701/213 |
| 6,251,048 | B1 | * | 6/2001  | Kaufman ........................... 482/8 |
| 6,388,613 | B1 | * | 5/2002  | Nagatsuma et al. ...... 342/357.08 |
| 6,463,385 | B1 | * | 10/2002 | Fry ................................. 701/213 |
| 6,702,719 | B1 | * | 3/2004  | Brown et al. ...................... 482/8 |
| 6,736,759 | B1 | * | 5/2004  | Stubbs et al. ...................... 482/8 |
| 6,837,827 | B1 |   | 1/2005  | Lee et al. |
| 7,220,220 | B2 | * | 5/2007  | Stubbs et al. .................... 482/72 |
| 7,254,516 | B2 | * | 8/2007  | Case et al. ...................... 702/182 |
| 7,398,151 | B1 | * | 7/2008  | Burrell et al. .................. 701/200 |
| 7,601,098 | B1 | * | 10/2009 | Lee et al. ........................... 482/8 |
| 7,607,243 | B2 | * | 10/2009 | Berner et al. .................... 36/136 |
| 7,670,263 | B2 | * | 3/2010  | Ellis et al. ......................... 482/8 |
| 2002/0160883 | A1 | * | 10/2002 | Dugan .............................. 482/8 |
| 2004/0046692 | A1 | * | 3/2004  | Robson et al. ............ 342/357.06 |
| 2004/0077462 | A1 |   | 4/2004  | Brown et al. |
| 2005/0148388 | A1 | * | 7/2005  | Vayra et al. ...................... 463/32 |
| 2005/0172311 | A1 |   | 8/2005  | Hjelt et al. |
| 2006/0030407 | A1 | * | 2/2006  | Thayer ............................ 463/42 |
| 2006/0095160 | A1 | * | 5/2006  | Orita et al. ...................... 700/248 |
| 2006/0234194 | A1 | * | 10/2006 | De Ley et al. ................. 434/169 |
| 2007/0111858 | A1 | * | 5/2007  | Dugan .............................. 482/8 |
| 2007/0213178 | A1 |   | 9/2007  | Lemmela |
| 2007/0287596 | A1 | * | 12/2007 | Case et al. ........................ 482/8 |

FOREIGN PATENT DOCUMENTS

| WO | 99/49279 | 9/1999 |
| WO | 2005098467 A2 | 10/2005 |

OTHER PUBLICATIONS

Korean Office Action dated Jan. 3, 2011.

* cited by examiner

Primary Examiner — Loan Thanh
Assistant Examiner — Daniel Roland
(74) Attorney, Agent, or Firm — Alston & Bird LLP

(57) ABSTRACT

A method for providing an exercise goal using an exercise data device, the method including: receiving input indicating a selected exercise goal; obtaining exercise goal data relating to the selected exercise goal; obtaining a current performance measurement related to exercise performance of a user of the exercise data device, the current performance measurement including a current distance and a current time measurement; calculating a current progress indicator using the current performance measurement and the exercise goal data; and providing the current progress indicator to the user.

30 Claims, 3 Drawing Sheets

EXERCISE DATA DEVICE, SERVER, SYSTEM AND METHOD

FIELD OF THE INVENTION

The aspects of the invention generally relate to exercise data devices and more particularly to user interfaces of exercise data devices.

BACKGROUND OF THE INVENTION

Mobile terminals, or mobile (cellular) telephones, for mobile telecommunications systems like GSM, UMTS, D-AMPS and CDMA2000 have been used for many years now. In the older days, mobile terminals were used almost exclusively for voice communication with other mobile terminals or stationary telephones. More recently, the use of modern terminals has been broadened to include not just voice communication, but also various other services and applications such as www/wap browsing, video telephony, electronic messaging (e.g. SMS, MMS, email, instant messaging), digital image or video recording, FM radio, music playback, exercise analysis, electronic games, calendar/organizer/time planner, word processing, etc. Furthermore, the modern terminals have local connectivity abilities, such as Bluetooth, allowing the mobile terminals to communicate with a wide array of devices.

One relatively new use of mobile terminals is to use them as exercise tracking devices. The terminal is then able to measure and record time and distance during exercise. However, users sometimes lack motivation to actually follow through and perform the exercise as originally intended.

In the prior art, one attempt to provide users with motivation to exercise is to collect statistical data, and thus be able to show to the user the amount of exercise that the user has performed, promoting further exercise. This may work to motivate the user in some cases, but often the user needs to be provided with a way to make it more fun to exercise.

Consequently, there is a need to provide an exercise data device and method providing motivation to users to exercise.

SUMMARY OF THE INVENTION

In view of the above, an objective of the invention is to solve or at least reduce the problems discussed above.

Generally, the above objectives are achieved by the attached independent patent claims.

According to a first aspect of the invention there has been provided a method for providing an exercise goal using an exercise data device, the method comprising: receiving input indicating a selected exercise goal; obtaining exercise goal data relating to the selected exercise goal; obtaining a current performance measurement related to exercise performance of a user of the exercise data device, the current performance measurement comprising a current distance and a current time measurement; calculating a current progress indicator using the current performance measurement and the exercise goal data; and providing the current progress indicator to the user.

The obtaining a current performance measurement, calculating a current progress indicator and providing the current progress indicator, may be repeated until an exercise associated with the exercise goal is determined to have ended.

The obtaining exercise goal data may involve obtaining exercise goal data relating to the selected exercise goal, the exercise goal data comprising at least one check point, each at least one check point comprising a check point time and a check point distance.

The exercise goal data may be related to previously measured performance measurements recorded in the exercise data device.

The exercise goal data may be related to performance measurements of another user.

The user may be associated with a current performance class, and the exercise goal data may be related to the user qualifying for a performance class being higher than current performance class.

The user may be associated with a current performance class, and the exercise goal data is calculated by the exercise data device using the current performance class as an input.

The method may furthermore comprise, prior to the calculating a current progress indicator, calculating a current target position using at least the exercise goal data and the current time measurement, wherein the current progress indicator may include a measurement indicating a current position of the user, in time, related the target position.

The method may furthermore comprise, prior to the calculating a current progress indicator, calculating a current target position using at least the exercise goal data and the current time measurement, wherein the current progress indicator may include a measurement indicating a current position of the user, in distance, related the target position.

The method may furthermore comprise, after an exercise associated with the exercise goal is determined to have ended: submitting performance data indicating a final result of the exercise goal over a network to a server.

The exercise goal may be related to running.

The exercise goal may be related to cycling.

The providing the current progress indicator to the user may involve presenting the current progress indicator on a display.

The providing the current progress indicator to the user may involve presenting at least part of the current progress indicator using voice synthesis.

A second aspect of the invention is an exercise data device configured to provide an exercise goal, the exercise data device comprising a controller, wherein: the controller is configured to receive input indicating a selected exercise goal; the controller is configured to obtain exercise goal data relating to the selected exercise goal; the controller is configured to obtain a current performance measurement related to exercise performance of a user of the exercise data device, the current performance measurement comprising a current distance and a current time measurement; the controller is configured to calculate a current progress indicator using the current performance measurement and the exercise goal data; and the controller is configured to provide the current progress indicator to the user.

The exercise data device may be a mobile communication terminal.

A third aspect of the invention is an exercise data device configured to provide an exercise goal, the exercise data device comprising: a controller; means for receiving input indicating a selected exercise goal; means for obtaining exercise goal data relating to the selected exercise goal; means for obtaining a current performance measurement related to exercise performance of a user of the exercise data device, the current performance measurement comprising a current distance and a current time measurement; means for calculating a current progress indicator using the current performance measurement and the exercise goal data; and means for providing the current progress indicator to the user.

The exercise data device may be a mobile communication terminal.

A fourth aspect of the invention is a system configured to provide an exercise goal to a user, the system comprising a server and an exercise data device, the exercise data device comprising: a controller; means for receiving input indicating a selected exercise goal; means for obtaining exercise goal data relating to the selected exercise goal; means for obtaining a current performance measurement related to exercise performance of a user of the exercise data device, the current performance measurement comprising a current distance and a current time measurement; means for calculating a current progress indicator using the current performance measurement and the exercise goal data; means for providing the current progress indicator to the user; means for submitting performance data indicating a final result of the exercise goal over a network to the server, and the server comprising: means for receiving performance data indicating a final result of the exercise goal over a network from the exercise data device.

A fifth aspect of the invention is a system comprising a server and an exercise data device, the system configured to provide an exercise goal to a user, wherein the exercise data device comprises: a controller; the controller being configured to receive input indicating a selected exercise goal; the controller being configured to obtain exercise goal data relating to the selected exercise goal; the controller being configured to obtain a current performance measurement related to exercise performance of a user of the exercise data device, the current performance measurement comprising a current distance and a current time measurement; the controller being configured to calculate a current progress indicator using the current performance measurement and the exercise goal data; the controller being configured to provide the current progress indicator to the user; and the controller being configured to submit performance data indicating a final result of the exercise goal over a network to the server, and the server comprises: a server data receiver; the server data receiver controller being configured to receive performance data indicating a final result of the exercise goal over the network from the exercise data device.

The exercise data device may be a mobile communication terminal.

The system may furthermore comprise an intermediate communication device, and the controller may be configured to send the performance data over a short range link to the intermediate communication device, the intermediate communication device being configured to forward the performance data to the server.

The intermediate communication device may be a personal computer.

The intermediate communication device may be a mobile communication terminal.

The server may furthermore comprise a data sender for sending exercise goal data over the network to the exercise data device, the exercise data device furthermore comprises a data receiver for receiving the exercise goal data over the network, wherein the exercise goal data is data relating to a competition.

The server may furthermore comprise a memory, the memory comprising data relating the user of the exercise data device with a performance class, and the exercise goal data may be related to the performance class.

A sixth aspect of the invention is a server configured to communicate with an exercise data device, and the server comprising: server data receiver for receiving performance data indicating a final result of an exercise goal over a network from the exercise data device.

The server may furthermore comprise server data sender for sending exercise goal data over the network to the exercise data device.

The server may furthermore comprise a memory, the memory comprising data relating a user of the exercise data device with a performance class, and the exercise goal data is related to the performance class.

A seventh aspect of the invention is a computer program product comprising software instructions that, when executed in an exercise data device, performs the method according to the first aspect.

Other objectives, features and advantages of the present invention will appear from the following detailed disclosure, from the attached dependent claims as well as from the drawings.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

Embodiments of the present invention will now be described in more detail, reference being made to the enclosed drawings, in which:

FIG. 2b is a schematic side view illustrating the mobile terminal in FIG. 2a.

FIGS. 5a-d are schematic diagram showing how exercise challenges are used in the mobile terminal of FIG. 2a.

DETAILED DESCRIPTION OF THE INVENTION

The aspects of the invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout.

Figure 1:
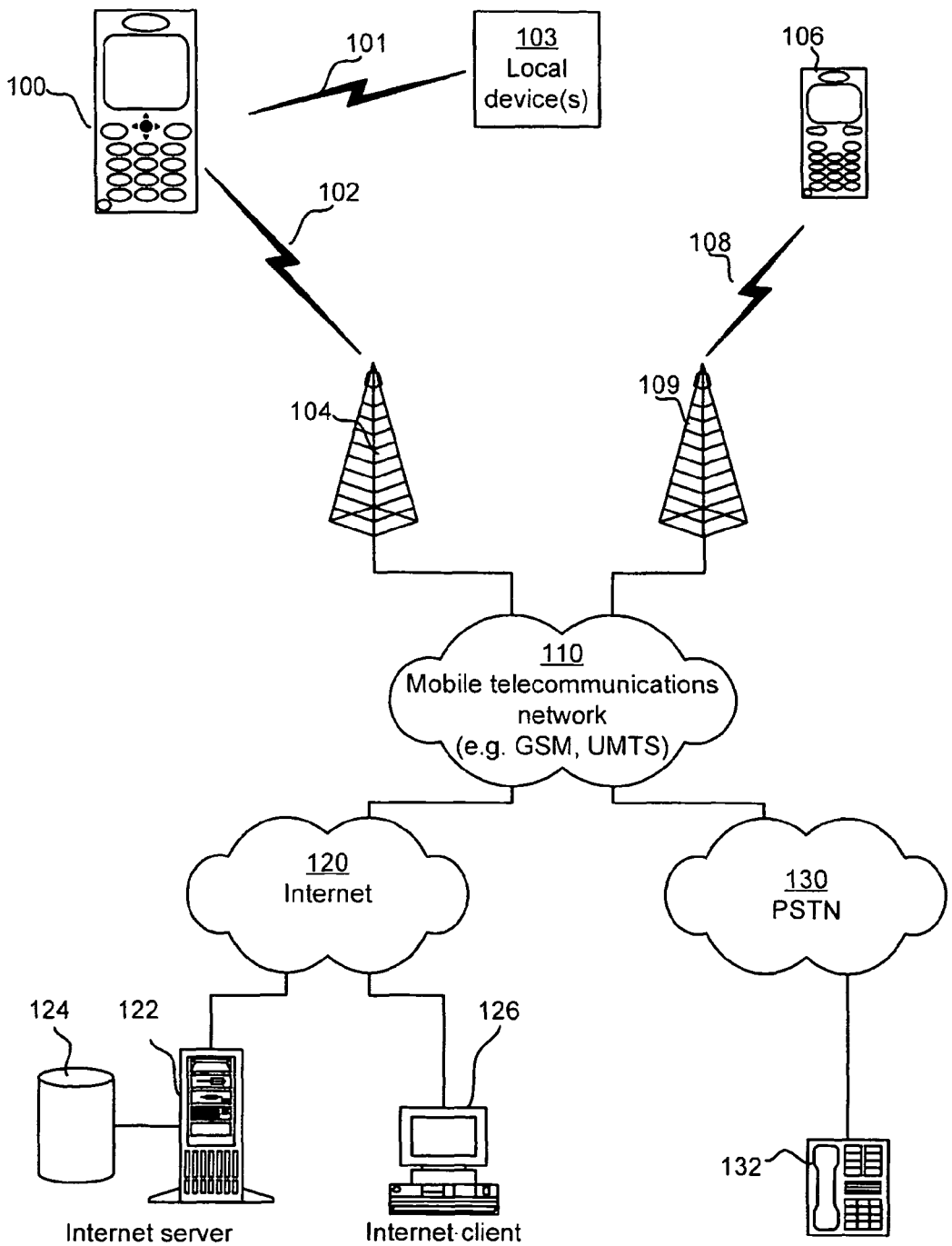
FIG. 1 is a schematic illustration of a cellular telecommunication system, as an example of an environment in which the present invention may be applied.

FIG. 1 illustrates an example of a cellular telecommunications system in which the invention may be applied. In the telecommunication system of FIG. 1, various telecommunications services such as cellular voice calls, www/wap browsing, cellular video calls, data calls, facsimile transmissions, music transmissions, still image transmissions, video transmissions, electronic message transmissions and electronic commerce may be performed between a mobile terminal 100 according to the present invention and other devices, such as another mobile terminal 106 or a stationary telephone 132. It is to be noted that for different embodiments of the mobile terminal 100 and in different situations, different ones of the telecommunications services referred to above may or may not be available; the invention is not limited to any particular set of services in this respect.

The mobile terminals 100, 106 are connected to a mobile telecommunications network 110 through RF links 102, 108 via base stations 104, 109. The mobile telecommunications network 110 may be in compliance with any commercially available mobile telecommunications standard, such as GSM, UMTS, D-AMPS, CDMA2000, FOMA and TD-SCDMA The mobile telecommunications network 110 is operatively connected to a wide area network 120, which may be Internet or a part thereof. An Internet server 122 has a data storage 124 and is connected to the wide area network 120, as is an Internet client computer 126. The server 122 may host a www/wap server capable of serving www/wap content to the mobile terminal 100.

A public switched telephone network (PSTN) 130 is connected to the mobile telecommunications network 110 in a familiar manner. Various telephone terminals, including the stationary telephone 132, are connected to the PSTN 130.

The mobile terminal 100 is also capable of communicating locally via a local link 101 to one or more local devices 103. The local link can be any type of link with a limited range, such as Bluetooth, a Universal Serial Bus (USB) link, a Wireless Universal Serial Bus (WUSB) link, an IEEE 802.11 wireless local area network link, an RS-232 serial link, etc. The local devices 103 can for example be various sensors that can communicate measurement values to the mobile terminal 100 over the local link 101.

Figure 2A:
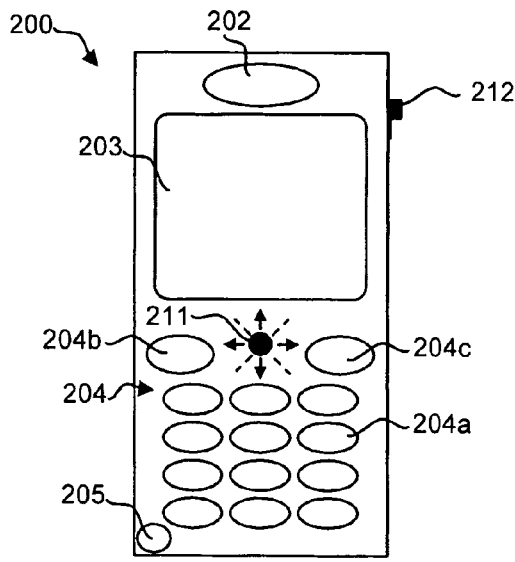
FIG. 2a is a schematic front view illustrating a mobile terminal according to an embodiment of the present invention.

An embodiment 200 of the mobile terminal 100 is illustrated in more detail in FIG. 2a. The mobile terminal 200 comprises a speaker or earphone 202, a microphone 205, a display 203 and a set of keys 204 which may include a keypad 204a of common ITU-T type (alpha-numerical keypad representing characters "0"-"9", "*" and "#") and certain other keys such as soft keys 204b, 204c and a joystick 211 or other type of navigational input device.

Figure 2B:
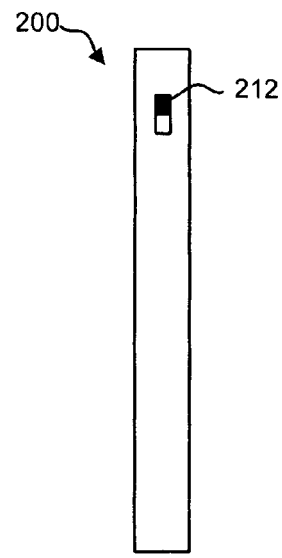

A mode switch button 212 is also provided, as can be seen more clearly in FIG. 2b. The button is used to switch an operating mode of the mobile terminal. In this embodiment, the button is by default positioned in an upper position. When the user wants to switch modes, the button is moved to a lower position and released, after which the button returns to the default upper position by mechanical means, such as a spring or similar. As the man skilled in the art will realize, the functionality of the mode switch button could easily be replaced with a push button or any other suitable type of input device.

Figure 3:
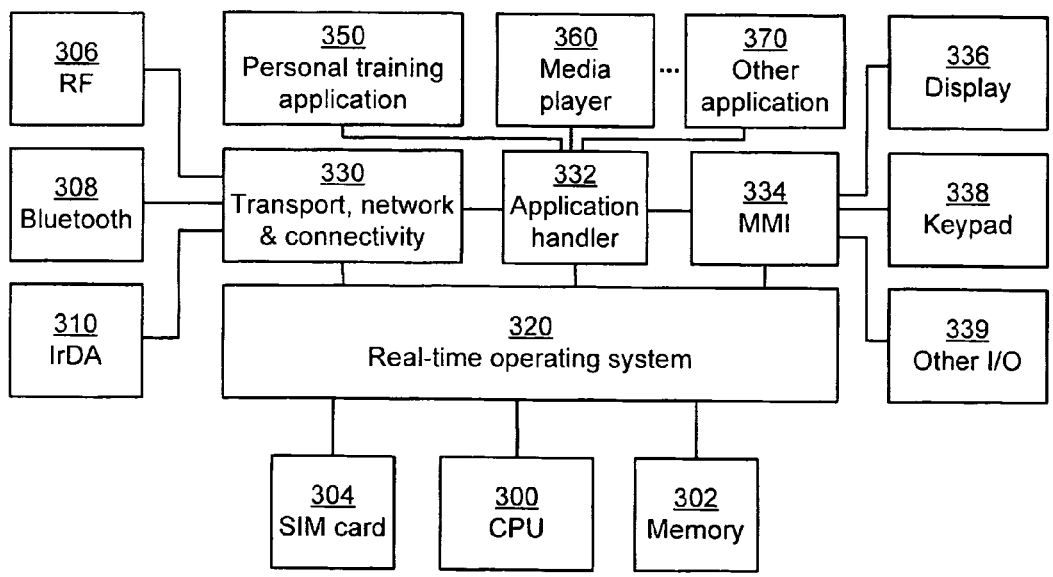
FIG. 3 is a schematic block diagram representing an internal component, software and protocol structure of the mobile terminal shown in FIGS. 2a and 2b.

The internal component, software and protocol structure of the mobile terminal 200 will now be described with reference to FIG. 3. The mobile terminal has a controller 300 which is responsible for the overall operation of the mobile terminal and is preferably implemented by any commercially available CPU ("Central Processing Unit"), DSP ("Digital Signal Processor") or any other electronic programmable logic device. The controller 300 has associated electronic memory 302 such as RAM memory, ROM memory, EEPROM memory, flash memory, or any combination thereof. The memory 302 is used for various purposes by the controller 300, one of them being for storing data and program instructions for various software in the mobile terminal. The software includes a real-time operating system 320, drivers for a man-machine interface (MMI) 334, an application handler 332 as well as various applications. The applications can include a personal exercise application 350, a media player application 360, as well as various other applications 370, such as applications for voice calling, video calling, sending and receiving SMS, MMS or email, web browsing, an instant messaging application, a phone book application, a calendar application, a control panel application, a camera application, one or more video games, a notepad application, etc.

The MMI 334 also includes one or more hardware controllers, which together with the MMI drivers cooperate with the display 336/203, keypad 338/204 as well as various other I/O devices such as microphone, speaker, vibrator, ringtone generator, LED indicator, etc. As is commonly known, the user may operate the mobile terminal through the man-machine interface thus formed.

The software also includes various modules, protocol stacks, drivers, etc., which are commonly designated as 330 and which provide communication services (such as transport, network and connectivity) for an RF interface 306, and optionally a Bluetooth interface 308 and/or an IrDA interface 310 for local connectivity. The RF interface 306 comprises an internal or external antenna as well as appropriate radio circuitry for establishing and maintaining a wireless link to a base station (e.g. the link 102 and base station 104 in FIG. 1). As is well known to a man skilled in the art, the radio circuitry comprises a series of analogue and digital electronic components, together forming a radio receiver and transmitter. These components include, i.a., band pass filters, amplifiers, mixers, local oscillators, low pass filters, AD/DA converters, etc.

The mobile terminal also has a SIM card 304 and an associated reader. As is commonly known, the SIM card 304 comprises a processor as well as local work and data memory.

Figure 4:
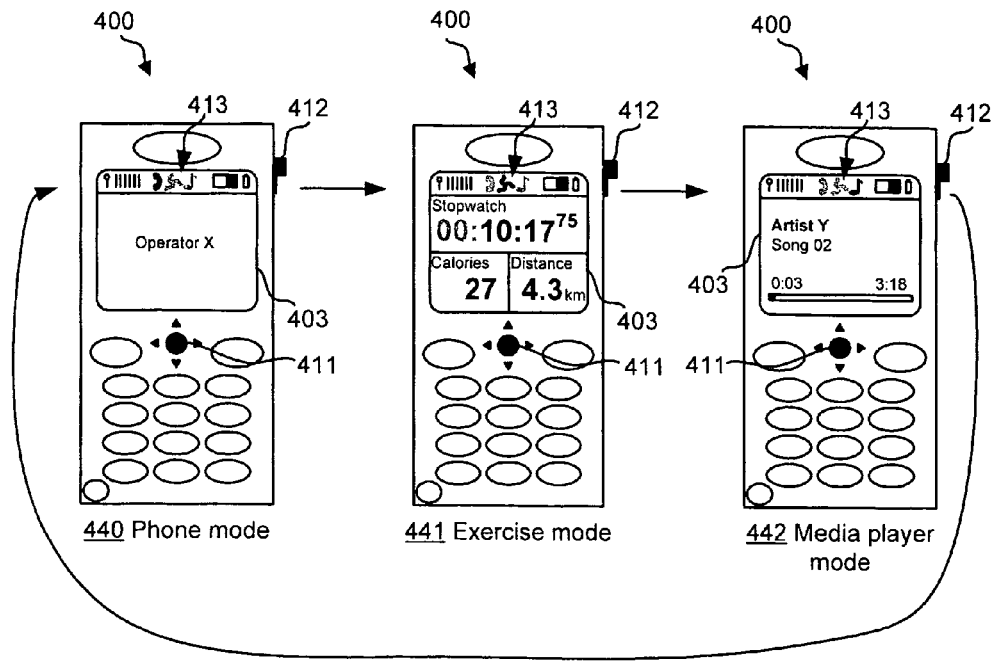
FIG. 4 is a schematic diagram showing how operational modes can be switched in an embodiment of the present invention.

FIG. 4 shows how operational modes can be switched in an embodiment of the present invention. The mobile terminal 400, such as mobile terminal 200 of FIG. 2a, comprises a display 403, such as display 203 of FIG. 2a, a joystick 411, such as joystick 211 of FIG. 2a, and a mode switch button 412 such as mode switch button 212 of FIG. 2a to allow the user to switch operational modes.

Operational modes are modes where the mobile terminal 400 behaves in a specific way. For example, FIG. 4 shows 3 operational modes: a phone mode 440, an exercise mode 441 and a media player mode 442.

When the mobile terminal 400 is in the phone mode 440, the mobile terminal behaves as a user would expect a regular mobile terminal to behave. In other words, a menu system and/or shortcuts allow the user to instruct the mobile terminal to perform a desired function, such as voice telephony, www/wap browsing, video telephony, electronic messaging (e.g. SMS, MMS, email, instant messaging), digital image or video recording, electronic games, calendar/organizer/time planner, word processing, etc.

When the mobile terminal 400 is in the exercise mode 441, the main purpose of the mobile terminal is to provide the user with applications related to the physical exercise of the user. The mobile terminal can in this mode support exercising such as running, cycling, etc.

In one embodiment, an accelerometer is integrated in the mobile terminal 400. In another embodiment, an external accelerometer is connected to the mobile terminal 400, e.g. over a local link, such as the local link 101 in FIG. 1. The accelerometer can detect acceleration and thereby steps that the user takes while the mobile terminal is carried by the user. When an accelerometer is integrated or connected to the mobile terminal 400, the mobile terminal automatically measures movement during the day. If the user previously has entered personal information, such as weight, height, etc., the mobile terminal 400 can convert the data from the accelerometer to other measurements, such as covered distance and burnt calories. Optionally, a GPS (Global Positioning System) sensor can be either integrated in, or connected to, the mobile terminal 400 to allow accurate distance measurement. Also, an external heart beat monitor can be connected to the mobile terminal 400 to detect heart beats and calculate heart rate.

When the mobile terminal 400 is in the media player mode 442, the main purpose of the mobile terminal is to play media to the user. For example, the media player can play music or sound files, such as MP3 (mpeg-1 audio layer 3) files, AAC (advanced audio coding) files or ogg files. Optionally, the media player can also be used to listen to FM (frequency modulated) radio, or to play video files according to standards such as MPEG-2, MPEG-4 or H.323.

As the user switches operational modes with mode switch button 412, the modes are switched serially. In the illustrated embodiment, there is a list of operational modes consisting of the phone mode 440, the exercise mode 441, and the media player mode 442, in that order. Consequently, if the mobile terminal 400 is in the phone mode 440 and the user actuates the mode switch button 412, the phone switches to the exercise mode 441. Similarly, if the mobile terminal 400 is in the exercise mode 441 and the user actuates the mode switch button 412, the phone switches to the media player mode 442. Finally, if the mobile terminal 400 is in the media player mode 443 and the user actuates the mode switch button 412, the phone loops back and switches to the phone mode 440.

To allow the user to easily determine what mode is currently used, elements of the user interface are specific for each mode. There are a multitude of distinguishing user interface elements that can vary to allow the user to see what mode is currently active, e.g., a centrally located light by the joystick 411 can change color, the background on the display 403 can have different colors or appearances, or the entire theme of the user interface with colors and fonts can change. In one embodiment, one of a set of icons at the top of the display 403 is highlighted to indicate which mode is active.

Mode changes can also change sound effects. For example in phone mode 440, the sounds may be discrete or even absent for actions such as button press, enter menu, exit menu, while in exercise mode 441, distinct and loud sounds are played for these actions to give clear feedback to the user while exercising. The media player mode 441 may have a totally different, more cool or ambient sound scheme on the actions mentioned in order to give feedback to the user on actions performed, while still not excessively disturbing the experience of listening to music. Optionally, the sound scheme can furthermore vary depending on whether headphones are connected to the mobile terminal 400 or not. The changes of sounds does not need to be totally different sounds; the changes could be effects applied to sounds. For example, a sound for a button press in phone mode could be reused in the media player mode, with a strong reverberation effect on it to give a more ambient effect while still providing familiarity to the user.

Additionally, a temporary user indication can be given when the actual mode change occurs. For example, the vibrator may vibrate on a mode change, where the vibration is either always identical for all modes or every mode has a particular vibration associated with it. Additionally, a dialog can show the name of the new operational mode in the display 403, or a sound effect or speech synthesizer pronouncing the new mode can be played to the user.

It is to be noted that although the modes can be switched certain appropriate processing of an inactive mode can still be performed. For example, the exercise application can count the steps of the user in the background, regardless of what mode the mobile terminal is in. Similarly, the media player can let the user hear an FM radio station while the mobile terminal is in exercise mode, or the phone application can temporarily interrupt current processing if there an incoming phone call is detected.

FIGS. 5*a-d* are schematic diagrams showing how exercise challenges are used in the mobile terminal of FIG. 2*a*.

Exercise challenges, or exercise goals, are all about pushing the user to exercise when the user lacks motivation, and also help to add variety to the process of getting fit, which can become boring. So, for example, after finishing an ordinary exercise, the user may choose to be challenged to a new activity.

Figure 5A:
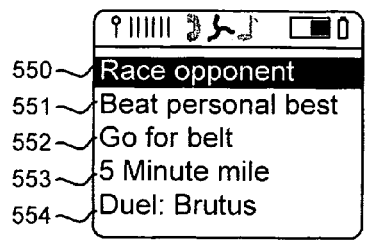

FIG. 5*a* shows a schematic screen layout where the user can select an exercise challenge corresponding to a menu item among a plurality of presented menu items 550-554. In this view there are five different exercise challenges available: race opponent 550, beat personal best 551, go for belt 552, 5 minute mile 553 and duel 554. The available challenges can depend on the current belt, or performance class, that is associated with the user. For example, the 5 minute mile challenge 553 can be shown only once the user has a belt at a level advanced enough for such a challenge to be appropriate.

Each one of these challenges has challenge data, or exercise goal data, associated with it, where the challenge data is used during the exercise challenge to define the goal and optionally intermediate points of the goal.

Once a menu item is selected, more details can be required from the user. For example, if the user selects beat personal best 551, the user is then prompted to select a track to try to beat. The tracks are previously defined by the user, typically having at least a track length and a name.

If go for belt 552 is selected, the user is presented with a challenge in order to gain the next higher belt. This may for example be to run a specific distance in a specific time or less.

Figure 5B:
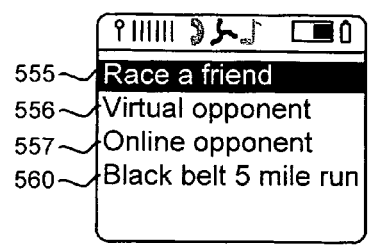

If race opponent 550 is selected, the user is presented with three more options, as can be seen in FIG. 5*b*. Here, within race opponent 550, the user can select to race a friend 555, a virtual opponent 556, an online opponent 557 or Black belt 5 mile run 560. Racing a friend 555 means the user races against another user of the same mobile terminal. A virtual opponent 556 is a fictive opponent stored in the mobile terminal. The virtual opponent 556 can be configured to run at a speed profile, having different speeds at different locations over a track, mimicking human behavior. For example, one particular opponent may be inclined to run very quickly to start with, but then slow down towards the end of the race. Optionally, the speed may be randomly slower or faster than the profile, providing an even more life-like opponent. The speed profile can be pre-configured in the terminal from the factory, or the user can configure the speed profile of a virtual opponent 556. Optionally, new virtual opponents can be downloaded from a server, such as server 122 of FIG. 1. An online opponent 557 is another user using a separate terminal, where the two terminals connect over a mobile telecommunications network, such as network 110 of FIG. 1, and optionally a wide area network, such as network 120 of FIG. 1, to exchange data during the challenge. In this way, two friends are able to compete against each other even though they may be in two separate locations, even two different countries.

The black belt 5 mile run 560 means that it is also possible to race against online opponents in a competition managed by a central server, such as server 122 of FIG. 1. For example, the challenge may be for all black belt holders in Sweden to run 5 miles on Sunday morning before 11 a.m. The challenge could be dynamically populated in the race opponent menu of 5B. Optionally, a message, such as an SMS or MMS could be sent out to all eligible contestants. Optionally, a reminder can also be sent out by the server 122 to the mobile terminal if the user has accepted the challenge, so that the user will not forget to participate in the competition. When the competition is available, such as on a Sunday morning, the menu item 560 for it is available in the race opponent menu. The user selects the menu item 560 for the competition and performs the run. Once the user has run the 5 miles, data is sent in from the mobile terminal to the server 122. This allows the server to collect the times for all the contestants and to determine a winner. The winner can be sent out as a message to all contestants, or it can be published on a web site. The server 122 can store in its memory the belt level for each user; whereby the result of the race can also affect the belt level.

Once a challenge is selected, and the user indicates that the exercising is to be started, the terminal regularly, such as once a second, performs a routine to update status.

The routine typically first calculates a current target position. This position is where the user should be in distance, at that particular time, if the user is exactly in line with the target. This position is typically calculated using an interpolation between two check points of the target. The check points are points of the target, each with a time and a distance, from which a profile of the target's position over time thus can be deduced.

Then the routine obtains a current performance measurement, including a current distance and a current time of the user.

Figure 5C:
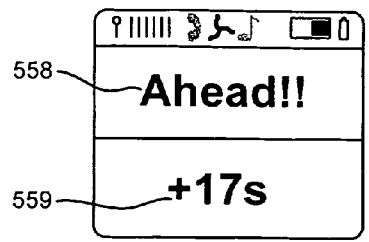
Figure 5D:
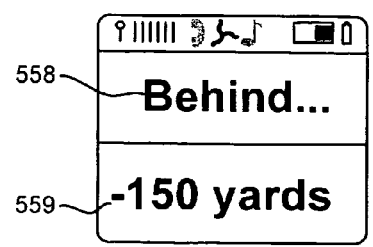

Once the current target position and the current performance measurement are available, a progress indicator can be calculated. For example, as is shown in FIG. 5c, a lower part 559 of the display shows a time based progress indicator, +17 s in this example. The upper part 558 shows, in this example, that the user is ahead of the target position. In FIG. 5d, a distance based progress indicator is shown in the lower part 559 of the display, in this instance showing that the user is 150 yards behind. At the same time, the upper part 558 shows clearly that the user is behind. The user can switch between time and distance based progress indicators, or other suitable progress indicators, at will. The units can be configured to be SI based units or imperial units, depending on the preferences of the user. Optionally, the data on the screen can be presented to the user by means of voice synthesis to a speaker or headphones, reducing the need for the user to take the concentration to look on the display to check the current position of the user. This may be triggered by the user tapping on the display, which is detected by an internal or attached accelerometer and interpreted by the controller as a user input to read out data of the current display screen.

Once the exercise challenge is over, data in the mobile terminal is updated as needed. This includes statistical data, e.g. to allow later analysis of average time to finish a particular track, and state data, e.g. a new belt awarded to the user, or a new personal best time on a track.

It is also to be noted that while the in the described embodiment, the exercise application is executed in a mobile terminal, the exercise application could be executed in any suitable portable exercise data device, e.g. a wrist-worn dedicated exercise device. If the exercise data device is not able to communicate directly with the server, the exercise data device can communicate with an intermediate device, such as a personal computer or mobile communication terminal, which in turn communicates with the server.

The invention has mainly been described above with reference to a few embodiments. However, as is readily appreciated by a person skilled in the art, other embodiments than the ones disclosed above are equally possible within the scope of the invention, as defined by the appended patent claims.

What is claimed is:

1. A method comprising:
receiving, by a cellular telecommunications network, at least one input in a portable device capable of executing an exercise application indicating a selected exercise goal;
obtaining, from the exercise application in the portable device, exercise goal data relating to said selected exercise goal;
obtaining a current performance measurement related to exercise performance data inputted to said exercise data device, said current performance measurement comprising a current distance and a current time measurement;
calculating a current progress indicator using said current performance measurement and said exercise goal data; and
using the current progress indicator to provide an indication of the current performance measurement relative to the selected exercise goal;
wherein said exercise goal data comprises at least one check point, each at least one check point comprising a check point time and a check point distance;
the selected exercise goal corresponds to a detected current performance class, and said exercise goal data is calculated by said exercise application in the portable device using said detected current performance class as an input;
wherein exercise goals enabled by the exercise application for selection are limited by a detected current performance class;
the method further comprising using the exercise goal data to define intermediate points for the selected exercise goal, and calculating a current target position using an interpolation between at least two intermediate points of the selected exercise goal to provide a profile of the current target position over time; and
comparing the profile of current target position over time to a profile of current target position over time of an online opponent at another portable device in real time and providing an indication of a result of the comparison on the current progress indicator; and
sending, by the cellular telecommunications network, the result of the comparison to the online opponent.

2. The method according to claim 1, wherein said obtaining a current performance measurement, calculating a current progress indicator and providing said current progress indicator, are repeated until an exercise associated with said exercise goal is determined to have ended.

3. The method according to claim 1, wherein said exercise goal data is related to previously measured performance measurements recorded in said exercise data device.

4. The method according to claim 1, wherein said exercise goal data is related to performance measurements of a user that is different than a current user of the exercise application.

5. The method according to claim 1, wherein a user is associated with a current performance class, and said exercise goal data is related to said user qualifying for a performance class being higher than a current performance class.

6. The method according to claim 1, furthermore comprising, prior to said calculating a current progress indicator, calculating a current target position using at least said exercise goal data and said current time measurement,
wherein said current progress indicator includes a measurement indicating a current position of a user, in time, related to said target position.

7. The method according to claim 1, furthermore comprising, prior to said calculating a current progress indicator, calculating a current target position using at least said exercise goal data and said current time measurement, wherein said current progress indicator includes a measurement indicating a current position of a user, in distance, related to said target position.

8. The method according to claim 1, furthermore comprising, after an exercise associated with said exercise goal is determined to have ended:

submitting performance data indicating a final result of said exercise goal over a network to a server.

9. The method according to claim 1, wherein said exercise goal is related to running.

10. The method according to claim 1, wherein said exercise goal is related to cycling.

11. The method according to claim 1, comprising providing a current progress indicator to a user and the online opponent includes presenting said current progress indicator on a display of each respective portable device.

12. The method according to claim 11, wherein providing said current progress indicator comprises presenting at least part of said current progress indicator using voice synthesis.

13. A computer program product comprising software instructions stored on a computer-readable storage medium that, when executed in an exercise data device, performs the method according to claim 1.

14. The method of claim 1 wherein exercise goals enabled by the exercise application for selection are dependent upon the detected current performance class.

15. The method of claim 14 wherein the detected current performance class is dependent upon prior exercise goals achieved by a user of the exercise application.

16. The method of claim 1 further comprising obtaining a current performance measurement and providing a progress indicator using the current performance measurement and the current target position of a user and the online opponent, the progress indicator being configured to provide a visual indication of the current performance measurement against the current target position of each of the user and the online opponent.

17. An exercise data device configured to provide an exercise goal, said exercise data device comprising a controller configured to perform the method of claim 1.

18. The exercise data device according to claim 17, wherein said exercise data device is a mobile communication terminal.

19. The exercise data device of claim 17 comprising:

means for receiving the at least one input for the application indicating a selected exercise goal;

means for obtaining the exercise goal data relating to said selected exercise goal;

means for obtaining the current performance measurement related to exercise performance;

means for calculating the current progress indicator using said current performance measurement and said exercise goal data; and means for providing said current progress indicator.

20. A system comprising a server and an exercise data device, said system configured to provide an exercise goal to a user, wherein said exercise data device comprises:

a controller configured to perform the method of claim 1;

said controller further configured to submit performance data indicating a final result of said exercise goal over a network to said server, and said server comprises:

a server data receiver with a controller;

said server data receiver controller being configured to receive performance data indicating a final result of said exercise goal over said network from said exercise data device.

21. The system of claim 20, comprising:

means for receiving the at least one input for the application indicating a selected exercise goal;

means for obtaining the exercise goal data relating to said selected exercise goal;

means for obtaining the current performance measurement related to exercise performance;

means for calculating the current progress indicator using said current performance measurement and said exercise goal data;

means for providing said current progress indicator.

22. The system according to claim 21, wherein said exercise data device is a mobile communication terminal.

23. The system according to claim 21, wherein said system furthermore comprises an intermediate communication device, and said controller is configured to send said performance data over a short range link to said intermediate communication device, said intermediate communication device being configured to forward said performance data to said server.

24. The system according to claim 23, wherein said intermediate communication device is a personal computer.

25. The system according to claim 23, wherein said intermediate communication device is a mobile communication terminal.

26. The system according to claim 23, wherein said server furthermore comprises a data sender for sending exercise goal data over said network to said exercise data device, said exercise data device furthermore comprises a data receiver for receiving said exercise goal data over said network, wherein said exercise goal data is data relating to a competition.

27. The system according to claim 26, wherein said server furthermore comprises a memory, said memory comprising data relating said user of said exercise data device with a performance class, and said exercise goal data is related to said performance class.

28. A server configured to communicate with an exercise data device, and said server comprising:

server data receiver for receiving performance data indicating a final result of an exercise goal over a network from said exercise data device, said exercise device comprising a controller for performing the method of claim 1.

29. The server according to claim 28, wherein said server furthermore comprises server data sender for sending the exercise goal data over said network to said exercise data device.

30. The server according to claim 29, wherein said server furthermore comprises a memory, said memory comprising data relating a user of said exercise data device with a performance class, and said exercise goal data is related to said performance class.

* * * * *